United States Patent
Bell et al.

(10) Patent No.: US 10,920,244 B2
(45) Date of Patent: Feb. 16, 2021

(54) COMPOSITIONS FOR TARGETING CONDUCTING AIRWAY CELLS COMPRISING ADENO-ASSOCIATED VIRUS CONSTRUCTS

(75) Inventors: Christie L Bell, Philadelphia, PA (US); James M Wilson, Glen Mills, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/266,599

(22) PCT Filed: Apr. 29, 2010

(86) PCT No.: PCT/US2010/032943
§ 371 (c)(1),
(2), (4) Date: Oct. 27, 2011

(87) PCT Pub. No.: WO2010/127097
PCT Pub. Date: Nov. 4, 2010

(65) Prior Publication Data
US 2012/0046349 A1     Feb. 23, 2012

Related U.S. Application Data

(60) Provisional application No. 61/174,149, filed on Apr. 30, 2009.

(51) Int. Cl.
| | | |
|---|---|---|
| *C12N 15/864* | (2006.01) | |
| *C12N 15/86* | (2006.01) | |
| *C12N 7/01* | (2006.01) | |
| *C12N 15/35* | (2006.01) | |
| *C12N 15/40* | (2006.01) | |
| *A61K 48/00* | (2006.01) | |

(52) U.S. Cl.
CPC .......... *C12N 15/86* (2013.01); *A61K 48/0075* (2013.01); *C07K 2319/01* (2013.01); *C12N 2750/14143* (2013.01); *C12N 2750/14145* (2013.01); *C12N 2810/6027* (2013.01)

(58) Field of Classification Search
CPC ...... C12N 15/8645; C12N 2750/14143; C12N 2750/14144; C12N 2750/14145; A61K 48/005; A61K 48/0075
See application file for complete search history.

(56) References Cited

U.S. PATENT DOCUMENTS

| 5,478,745 | A | 12/1995 | Samulski et al. |
|---|---|---|---|
| 5,658,785 | A | 8/1997 | Johnson |
| 7,906,111 | B2 | 3/2011 | Wilson et al. |
| 2003/0138772 | A1 | 7/2003 | Gao et al. |
| 2006/0188483 | A1* | 8/2006 | Rabinowitz et al. ......... 424/93.2 |
| 2007/0092866 | A1* | 4/2007 | Bossis et al. ..................... 435/5 |
| 2009/0197338 | A1* | 8/2009 | Vandenberghe et al. ..... 435/471 |
| 2011/0151434 | A1 | 6/2011 | Gao et al. |
| 2011/0236353 | A1 | 9/2011 | Wilson et al. |
| 2011/0263027 | A1 | 10/2011 | Gao et al. |

FOREIGN PATENT DOCUMENTS

| CA | 2406745 | 1/2006 |
|---|---|---|
| EP | 1310571 | 2/2006 |
| EP | 2412721 A1 | 2/2012 |
| EP | 2425000 B1 | 2/2019 |
| JP | 2007/507223 | 3/2007 |
| WO | WO-97/17458 | 5/1997 |
| WO | WO-98/10088 | 3/1998 |
| WO | WO-99/15685 | 4/1999 |
| WO | WO-2003/042397 | 5/2003 |
| WO | WO 2005/033321 A | 4/2005 |
| WO | WO 2006/110689 A2 | 10/2006 |
| WO | WO-2008/027084 | 3/2008 |

OTHER PUBLICATIONS

Hauck et al, Characterization of Tissue Tropism Determinants of Adeno-Associated Virus Type 1, Journal of Virology, Feb. 2003, p. 2768-2774.*
Yang et al, A myocardium tropic adeno-associated virus (AAV) evolved by DNA shuffling and in vivo selection, PNAS, 2009, pp. 1-6.*
Limberis et al, Transduction Efficiencies of Novel AAV Vectors in Mouse Airway Epithelium In Vivo and Human Ciliated Airway Epithelium In Vitro, Molecular Therapy.org vol. 17 No. 2, 294-301 Feb. 2009.*

(Continued)

*Primary Examiner* — Maria Marvich
(74) *Attorney, Agent, or Firm* — Howson & Howson LLP; Colleen M. Schaller

(57) ABSTRACT

An artificial AAV capsid comprising a heterologous conducting airway targeting sequence is provided. The artificial AAV is useful as a targeting moiety, for delivery of heterologous molecules which are associated therewith. The artificial AAV is also useful in the generation of AAV vectors having the artificial capsid. Also described are methods of modifying the native tropism and transduction efficiency of vectors by improving and/or ablating their ability to transduce conducting airway cells. Methods of targeting conducting airway cells and delivering therapeutic and other molecules thereto are also provided.

14 Claims, 2 Drawing Sheets

Figure 1A:
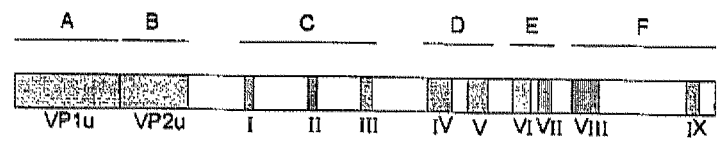

Specification includes a Sequence Listing.

(56) References Cited

OTHER PUBLICATIONS

Bell et al, Identification of a Domain of the AAV Capsid that Confers Transduction of Conducting Airway Epithelium, Gene Therapy Program, University of Pennsylvania, ASGCT 12$^{th}$ Annual Meeting of the American Society of Gene Therapy, (May 27-30, 2009) Abstract, e-published May 1, 2009.

Diprimio et al, Surface Loop Dynamics in Adeno-Associated Virus Capsid Assembly, Journal of Virology, 82(11):5178-5189, (Jun. 2008).

Flotte et al, Viral Vector-Mediated and Cell-Based Therapies for Treatment of Cystic Fibrosis, Molecular Therapy: The Journal of the American Society of Gene Therapy, 15(2):229-241, (Feb. 2007).

Gao et al, Adeno-Associated Viruses Undergo Substantial Evolution in Primates during Natural Infections, Journal of Virology, 100(10):6081-6086, (May 2003), Epublication Apr. 25, 2003.

Gao et al, Clades of Adeno-Associated Viruses are Widely Disseminated in Human Tissues, Journal of Virology, 78(12):6381-6388, (Jun. 2004).

Govindasamy et al, Structurally Mapping the Diverse Phenotype of Adeno-Associated Virus Serotype 4, Journal of Virology, 80(23):11556-70. (Dec. 2006) Epublication Sep. 13, 2006.

Greiger et al, Separate Basic Region Motifs within the Adeno-Associated Virus Capsid Proteins are Essential for Infectivity and Assembly, Journal of Virology, 80(11):5199-210, (Jun. 2006).

Halbert, et al, AAV-Mediated Gene Transfer to Mouse Lungs, Methods in Molecular Biology, 246:201-212, (2004).

Halbert, et al, Adeno-Associated Virus Type 6 (AAV6) Vectors Mediate Efficient Transduction of Airway Epithelial Cells in Mouse Lungs Compared to that of AAV2 Vectors, Journal of Virology, 75(14):6615-6624, (Jul. 2001).

Halbert et al, Repeat Transduction in the mouse Lung by using Adeno-Associated Virus Vectors with Different Serotypes, 74(3):1524-1532, (Feb. 2000).

Kronenberg et al, A Conformational Change in the Adeno-Associated Virus Type 2 Capsid Leads to the Exposure of Hidden VP1 N Termini, Journal of Virology, 79(9):5296-303, (May 2005).

Limberis, et al, Transduction Efficiencies of Novel AAV Vectors in Mouse Airway Epithelium in Vitro, Molecular Therapy, 17(2):294-301, (Feb. 2009).

Nam et al, Structure of Adeno-Associated Virus Serotype 8, a Gene Therapy Vector, Journal of Virology, 81(22):12260-12271, (Nov. 2007).

Oral Presentation, May 29, 2009 @ 12$^{th}$ Annual Meeting of American Society of Gene & Cell Therapy, May 27-30, 2009, San Diego, California.

Padron et al, Structure of Adeno-Associated Virus Type 4, Journal of Virology, 79(8):5047-58, (Apr. 2005).

Rutledge et al, Infectious Clones and Vectors Derived from Adeno-Associated Virus (AAV) Serotypes Other Than AAV Type 2, Journal of Virology, 72(1):309-319, (Jan. 1998).

Shen, et al, Characterization of the Relationship of AAV Capsid Domain Swapping to Liver Transduction Efficiency, Molecular Therapy: The Journal of the American Society of Gene Therapy, 15(11):1955-1962, (Nov. 2007).

Sonntag et al, Adeno-Associated Virus Type 2 Capsids with Externalized VP1/VP2 Trafficking Domains are Generated Prior to Passage through the Cytoplasm and are Maintained until Uncoating Occurs in the Nucleus, Journal of Virology, 80(22):11040-54. (Nov. 2006), Epublication Sep. 6, 2006.

Xie et al, The Atomic Structure of Adeno-Associated Virus (AAV-2), a Vector for Human Gene Therapy, Proceedings of the National Academy of Sciences of United States of America, 99(16):10405-10410. (Aug. 2002), E publication Jul. 22, 2002.

Yang, et al, Virus-Mediated Transduction of Murine Retina with Adeno-Associated Virus: Effects of Viral Capsid and Genome Size, Journal of Virology: The American Society for Microbiology, 76(15):7651-7660, (Aug. 1, 2002).

Aneja, MK and Rudolph, C., Gene Therapy of Surfactant Protein B Deficiency, Current Opinion of Molecular Therapy, 8(5):432-438, (Oct. 2006).

Cruz et al, The Promise of Gene Therapy for the Treatment of Alpha-1 Antitrypsin Deficiency, Pharmacogenomics, 8(9):1191-1198, (Sep. 2007).

Bell, Christie, L., Virus-cell interactions necessary for adeno-associated virus vector-mediated gene delivery to the conducting airway epithelium (Jan. 1, 2011). Abstract of Dissertation, available from ProQuest, Paper AAI3497965, http:/repository.upenn.edu/dissertations/AAI3497965.

Bell, Christie L., Dissertation, Virus-cell interactions necessary for adeno-associated virus vector-mediated gene delivery to the conducting airway epithelium (Jan. 1, 2011), p. 1-124.

Yang, et al. "A myocardium tropic adeno-associated virus (AAV) evolved by DNA shuffling and in vivo selection." Proceedings of the National Academy of Sciences 106.10 (2009): 3946-3951. (Mar. 2009).

Boshart, et al., A very strong enhancer is located upstream of an immediate early gene of human cytomegalovirus. Cell. Jun. 1985;41(2):521-530. (Jun. 1985).

Chatterji, et al., Chemical conjugation of heterologous proteins on the surface of Cowpea mosaic virus. Bioconj Chem ; 15(4):807-813 (Jul. 2004).

Destito, et al., Folic acid-mediated targeting of cowpea mosaic virus particles to tumor cells. Chem Biol Oct. 2007; 14(10):1152-1162 (Oct. 2007).

Fisher, et al., Transduction with recombinant adeno-associated virus for gene therapy is limited by leading-strand synthesis. J. Virol., Jan. 1996;70(1):520-532. (Jan. 1996).

Gossen, et al., Tight control of gene expression in mammalian cells by tetracycline-responsive promoters. Proc Natl Acad Sci U S A. Jun. 15, 1992;89(12):5547-5551. (Jun. 1992).

Gossen, et al., Transcriptional activation by tetracyclines in mammalian cells. Science, Jun. 23, 1995;268(5218):1766-1769. (Jun. 1995).

Gray, et al., Mucociliary differentiation of serially passaged normal human tracheobronchial epithelial cells. Am J Respir Cell Mol Biol, Jan. 1996;14(1):104-12. (Jan. 1996).

Harvey, et al., Inducible control of gene expression: prospects for gene therapy. Curr. Opin. Chem. Biol., Aug. 1998;2(4):512-518. (Aug. 1998).

Magari, et al., Pharmacologic control of a humanized gene therapy system implanted into nude mice. J. Clin. Invest., Dec. 1, 1997;100(11):2865-72. (Dec. 1997).

No, et al., Ecdysone-inducible gene expression in mammalian cells and transgenic mice. Proc. Natl. Acad. Sci. USA, Apr. 16, 1996;93(8):3346-51. (Apr. 1996).

Oh, et al., Folate immobilized and PEGylated adenovirus for retargeting to tumor cells. Bioconjug Chem 2006; 17(3):721-727 (May 2006).

Thomson et al., A comprehensive comparison of multiple sequence alignments, Nucleic Acids Res. Jul. 1, 1999;27(13):2682-2690 (Jul. 1999).

Wang, et al., Ligand-inducible and liver-specific target gene expression in transgenic mice. Nat Biotechnol. Mar. 1997;15(3):239-243. (Mar. 1997).

Wang, et al., Positive and negative regulation of gene expression in eukaryotic cells with an inducible transcriptional regulator. Gene Ther. May 1997;4(5):432-441. (May 1997).

* cited by examiner

SEQUENCE LISTING

```
<160> NUMBER OF SEQ ID NOS: 38

<210> SEQ ID NO 1
<211> LENGTH: 736
<212> TYPE: PRT
<213> ORGANISM: Unknown
<220> FEATURE:
<223> OTHER INFORMATION: capsid of adeno-associated virus 6

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80
```

```
Gln Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Phe Gly Leu Val Glu Glu Gly Ala Lys Thr Ala Pro Gly Lys Lys Arg
            130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
            165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
            195                 200                 205

Ala Pro Met Ala Asp Asn Asn Glu Gly Ala Asp Gly Val Gly Asn Ala
            210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
            290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
            325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
            405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
            450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495
```

-continued

```
Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
    515                 520                 525

Asp Asp Lys Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 2
<211> LENGTH: 736
<212> TYPE: PRT
<213> ORGANISM: Unknown
<220> FEATURE:
<223> OTHER INFORMATION: capsid of adeno-associated virus 9

<400> SEQUENCE: 2

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125
```

```
Leu Gly Leu Val Glu Glu Ala Ala Lys Thr Ala Pro Gly Lys Lys Arg
    130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
        195                 200                 205
Ala Pro Val Ala Asp Asn Asn Glu Gly Ala Asp Gly Val Gly Ser Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
            260                 265                 270
Ala Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
        355                 360                 365
Ala Asp Val Phe Met Ile Pro Gln Tyr Gly Tyr Leu Thr Leu Asn Asp
    370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
        435                 440                 445
Lys Thr Ile Asn Gly Ser Gly Gln Asn Gln Gln Thr Leu Lys Phe Ser
    450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
            500                 505                 510
Gly Arg Asn Ser Leu Met Asn Pro Gly Pro Ala Met Ala Ser His Lys
        515                 520                 525
Glu Gly Glu Asp Arg Phe Phe Pro Leu Ser Gly Ser Leu Ile Phe Gly
    530                 535                 540
Lys Gln Gly Thr Gly Arg Asp Asn Val Asp Ala Asp Lys Val Met Ile
```

```
                545                 550                 555                 560
Thr Asn Glu Glu Ile Lys Thr Thr Asn Pro Val Ala Thr Glu Ser
                    565                 570                 575
Tyr Gly Gln Val Ala Thr Asn His Gln Ser Ala Gln Ala Gln Ala Gln
                580                 585                 590
Thr Gly Trp Val Gln Asn Gln Gly Ile Leu Pro Gly Met Val Trp Gln
                595                 600                 605
Asp Arg Asp Val Tyr Leu Gln Gly Pro Ile Trp Ala Lys Ile Pro His
                610                 615                 620
Thr Asp Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                        645                 650                 655
Asp Pro Pro Thr Ala Phe Asn Lys Asp Lys Leu Asn Ser Phe Ile Thr
                    660                 665                 670
Gln Tyr Ser Thr Gly Gln Val Ser Val Glu Ile Glu Trp Glu Leu Gln
                    675                 680                 685
Lys Glu Asn Ser Lys Arg Trp Asn Pro Glu Ile Gln Tyr Thr Ser Asn
                690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
                        725                 730                 735
```

<210> SEQ ID NO 3
<211> LENGTH: 736
<212> TYPE: PRT
<213> ORGANISM: Unknown
<220> FEATURE:
<223> OTHER INFORMATION: capsid of adeno-associated virus 1

<400> SEQUENCE: 3

```
Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
                20                  25                  30
Lys Ala Asn Gln Gln Lys Gln Asp Asp Gly Arg Gly Leu Val Leu Pro
            35                  40                  45
Gly Tyr Lys Tyr Leu Gly Pro Phe Asn Gly Leu Asp Lys Gly Glu Pro
        50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
                100                 105                 110
Asn Leu Gly Arg Ala Val Phe Gln Ala Lys Lys Arg Val Leu Glu Pro
            115                 120                 125
Leu Gly Leu Val Glu Glu Gly Ala Lys Thr Ala Pro Gly Lys Lys Arg
        130                 135                 140
Pro Val Glu Gln Ser Pro Gln Glu Pro Asp Ser Ser Ser Gly Ile Gly
145                 150                 155                 160
Lys Thr Gly Gln Gln Pro Ala Lys Lys Arg Leu Asn Phe Gly Gln Thr
                165                 170                 175
Gly Asp Ser Glu Ser Val Pro Asp Pro Gln Pro Leu Gly Glu Pro Pro
```

-continued

```
                180                 185                 190
Ala Thr Pro Ala Ala Val Gly Pro Thr Thr Met Ala Ser Gly Gly Gly
            195                 200                 205
Ala Pro Met Ala Asp Asn Asn Glu Gly Ala Asp Gly Val Gly Asn Ala
210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ala Ser Thr Gly Ala Ser Asn Asp Asn His
            260                 265                 270
Tyr Phe Gly Tyr Ser Thr Pro Trp Gly Tyr Phe Asp Phe Asn Arg Phe
        275                 280                 285
His Cys His Phe Ser Pro Arg Asp Trp Gln Arg Leu Ile Asn Asn Asn
    290                 295                 300
Trp Gly Phe Arg Pro Lys Arg Leu Asn Phe Lys Leu Phe Asn Ile Gln
305                 310                 315                 320
Val Lys Glu Val Thr Thr Asn Asp Gly Val Thr Thr Ile Ala Asn Asn
                325                 330                 335
Leu Thr Ser Thr Val Gln Val Phe Ser Asp Ser Glu Tyr Gln Leu Pro
            340                 345                 350
Tyr Val Leu Gly Ser Ala His Gln Gly Cys Leu Pro Pro Phe Pro Ala
        355                 360                 365
Asp Val Phe Met Ile Pro Gln Tyr Gly Tyr Leu Thr Leu Asn Asn Gly
    370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Thr Phe Ser Tyr Thr Phe
                405                 410                 415
Glu Glu Val Pro Phe His Ser Ser Tyr Ala His Ser Gln Ser Leu Asp
            420                 425                 430
Arg Leu Met Asn Pro Leu Ile Asp Gln Tyr Leu Tyr Tyr Leu Asn Arg
        435                 440                 445
Thr Gln Asn Gln Ser Gly Ser Ala Gln Asn Lys Asp Leu Leu Phe Ser
    450                 455                 460
Arg Gly Ser Pro Ala Gly Met Ser Val Gln Pro Lys Asn Trp Leu Pro
465                 470                 475                 480
Gly Pro Cys Tyr Arg Gln Gln Arg Val Ser Lys Thr Lys Thr Asp Asn
                485                 490                 495
Asn Asn Ser Asn Phe Thr Trp Thr Gly Ala Ser Lys Tyr Asn Leu Asn
            500                 505                 510
Gly Arg Glu Ser Ile Ile Asn Pro Gly Thr Ala Met Ala Ser His Lys
        515                 520                 525
Asp Asp Glu Asp Lys Phe Phe Pro Met Ser Gly Val Met Ile Phe Gly
    530                 535                 540
Lys Glu Ser Ala Gly Ala Ser Asn Thr Ala Leu Asp Asn Val Met Ile
545                 550                 555                 560
Thr Asp Glu Glu Glu Ile Lys Ala Thr Asn Pro Val Ala Thr Glu Arg
                565                 570                 575
Phe Gly Thr Val Ala Val Asn Phe Gln Ser Ser Ser Thr Asp Pro Ala
            580                 585                 590
Thr Gly Asp Val His Ala Met Gly Ala Leu Pro Gly Met Val Trp Gln
        595                 600                 605
```

```
Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
        690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 4
<211> LENGTH: 75
<212> TYPE: PRT
<213> ORGANISM: Unknown
<220> FEATURE:
<223> OTHER INFORMATION: AAV clade A capsid fragment

<400> SEQUENCE: 4

Asn Arg Thr Gln Asn Gln Ser Gly Ser Ala Gln Asn Lys Asp Leu Leu
1               5                   10                  15

Phe Ser Arg Gly Ser Pro Ala Gly Met Ser Val Gln Pro Lys Asn Trp
            20                  25                  30

Leu Pro Gly Pro Cys Tyr Arg Gln Gln Arg Val Ser Lys Thr Lys Thr
        35                  40                  45

Asp Asn Asn Asn Ser Asn Phe Thr Trp Thr Gly Ala Ser Lys Tyr Asn
    50                  55                  60

Leu Asn Gly Arg Glu Ser Ile Ile Asn Pro Gly
65                  70                  75

<210> SEQ ID NO 5
<211> LENGTH: 23
<212> TYPE: DNA
<213> ORGANISM: Unknown
<220> FEATURE:
<223> OTHER INFORMATION: primer based on adeno-associated virus 6

<400> SEQUENCE: 5
agcctggacc grctratgaa tcc                                         23

<210> SEQ ID NO 6
<211> LENGTH: 23
<212> TYPE: DNA
<213> ORGANISM: Unknown
<220> FEATURE:
<223> OTHER INFORMATION: primer based on adeno-associated virus 6

<400> SEQUENCE: 6
gccatagcag gtccagggtt gat                                         23

<210> SEQ ID NO 7
<211> LENGTH: 25
<212> TYPE: DNA
<213> ORGANISM: Unknown
```

```
<220> FEATURE:
<223> OTHER INFORMATION: primer based on adeno-associated virus 9

<400> SEQUENCE: 7
agacgcggaa gcttcgatca actac                                         25

<210> SEQ ID NO 8
<211> LENGTH: 23
<212> TYPE: DNA
<213> ORGANISM: Unknown
<220> FEATURE:
<223> OTHER INFORMATION: primer based on adeno-associated virus 9

<400> SEQUENCE: 8
ggattcatya gycggtccag gct                                           23

<210> SEQ ID NO 9
<211> LENGTH: 23
<212> TYPE: DNA
<213> ORGANISM: Unknown
<220> FEATURE:
<223> OTHER INFORMATION: primer based on adeno-associated virus 9

<400> SEQUENCE: 9
atcaaccctg gacctgctat ggc                                           23

<210> SEQ ID NO 10
<211> LENGTH: 25
<212> TYPE: DNA
<213> ORGANISM: Unknown
<220> FEATURE:
<223> OTHER INFORMATION: primer based on adeno-associated virus 9

<400> SEQUENCE: 10
acctctagtc ctgcaggttt aaacg                                         25

<210> SEQ ID NO 11
<211> LENGTH: 25
<212> TYPE: DNA
<213> ORGANISM: Unknown
<220> FEATURE:
<223> OTHER INFORMATION: primer based on adeno-associated virus 9

<400> SEQUENCE: 11
agacgcggaa gcttcgatca actac                                         25

<210> SEQ ID NO 12
<211> LENGTH: 29
<212> TYPE: DNA
<213> ORGANISM: Unknown
<220> FEATURE:
<223> OTHER INFORMATION: primer based on adeno-associated virus 9

<400> SEQUENCE: 12
tccggactga ttctgagtct ttgagagat                                     29

<210> SEQ ID NO 13
<211> LENGTH: 29
<212> TYPE: DNA
<213> ORGANISM: Unknown
<220> FEATURE:
<223> OTHER INFORMATION: primer based on adeno-associated virus 6

<400> SEQUENCE: 13
atctctcaaa gactcagaat cagtccgga                                     29
```

```
<210> SEQ ID NO 14
<211> LENGTH: 23
<212> TYPE: DNA
<213> ORGANISM: Unknown
<220> FEATURE:
<223> OTHER INFORMATION: primer based on adeno-associated virus 6

<400> SEQUENCE: 14
acagccatgt tagctggaga ccc                                           23

<210> SEQ ID NO 15
<211> LENGTH: 23
<212> TYPE: DNA
<213> ORGANISM: Unknown
<220> FEATURE:
<223> OTHER INFORMATION: primer based on adeno-associated virus 9

<400> SEQUENCE: 15
gggtctccag ctaacatggc tgt                                           23

<210> SEQ ID NO 16
<211> LENGTH: 27
<212> TYPE: DNA
<213> ORGANISM: Unknown
<220> FEATURE:
<223> OTHER INFORMATION: primer based on adeno-associated virus 9

<400> SEQUENCE: 16
tagaaacgcg ctgttgtcgg tagctgg                                       27

<210> SEQ ID NO 17
<211> LENGTH: 23
<212> TYPE: DNA
<213> ORGANISM: Unknown
<220> FEATURE:
<223> OTHER INFORMATION: primer based on adeno-associated virus 6

<400> SEQUENCE: 17
gctaccgaca acagcgcgtt tct                                           23

<210> SEQ ID NO 18
<211> LENGTH: 25
<212> TYPE: DNA
<213> ORGANISM: Unknown
<220> FEATURE:
<223> OTHER INFORMATION: primer based on adeno-associated virus 6

<400> SEQUENCE: 18
ccaagaagaa gcaccagtcc aggta                                         25

<210> SEQ ID NO 19
<211> LENGTH: 25
<212> TYPE: DNA
<213> ORGANISM: Unknown
<220> FEATURE:
<223> OTHER INFORMATION: primer based on adeno-associated virus 9

<400> SEQUENCE: 19
tacctggact ggtgcttctt cttgg                                         25

<210> SEQ ID NO 20
<211> LENGTH: 25
<212> TYPE: DNA
<213> ORGANISM: Unknown
<220> FEATURE:
<223> OTHER INFORMATION: primer based on adeno-associated virus 9
```

<400> SEQUENCE: 20
acctctagtc ctgcaggttt aaacg                                              25

<210> SEQ ID NO 21
<211> LENGTH: 25
<212> TYPE: DNA
<213> ORGANISM: Unknown
<220> FEATURE:
<223> OTHER INFORMATION: primer based on adeno-associated virus 9

<400> SEQUENCE: 21
agacgcggaa gcttcgatca actac                                              25

<210> SEQ ID NO 22
<211> LENGTH: 29
<212> TYPE: DNA
<213> ORGANISM: Unknown
<220> FEATURE:
<223> OTHER INFORMATION: primer based on adeno-associated virus 9

<400> SEQUENCE: 22
tccggactga ttctgagtct ttgagagat                                          29

<210> SEQ ID NO 23
<211> LENGTH: 29
<212> TYPE: DNA
<213> ORGANISM: Unknown
<220> FEATURE:
<223> OTHER INFORMATION: primer based on adeno-associated virus 6

<400> SEQUENCE: 23
atctctcaaa gactcagaat cagtccgga                                          29

<210> SEQ ID NO 24
<211> LENGTH: 23
<212> TYPE: DNA
<213> ORGANISM: Unknown
<220> FEATURE:
<223> OTHER INFORMATION: primer based on adeno-associated virus 6

<400> SEQUENCE: 24
acagccatgt tagctggaga ccc                                                23

<210> SEQ ID NO 25
<211> LENGTH: 23
<212> TYPE: DNA
<213> ORGANISM: Unknown
<220> FEATURE:
<223> OTHER INFORMATION: primer based on adeno-associated virus 9

<400> SEQUENCE: 25
gggtctccag ctaacatggc tgt                                                23

<210> SEQ ID NO 26
<211> LENGTH: 25
<212> TYPE: DNA
<213> ORGANISM: Unknown
<220> FEATURE:
<223> OTHER INFORMATION: primer based on adeno-associated virus 9

<400> SEQUENCE: 26
acctctagtc ctgcaggttt aaacg                                              25

<210> SEQ ID NO 27

```
<211> LENGTH: 25
<212> TYPE: DNA
<213> ORGANISM: Unknown
<220> FEATURE:
<223> OTHER INFORMATION: primer based on adeno-associated virus 9

<400> SEQUENCE: 27
agacgcggaa gcttcgatca actac                                              25

<210> SEQ ID NO 28
<211> LENGTH: 26
<212> TYPE: DNA
<213> ORGANISM: Unknown
<220> FEATURE:
<223> OTHER INFORMATION: primer based on adeno-associated virus 9

<400> SEQUENCE: 28
tagaaacgcg ctgttgtcgg tagctg                                             26

<210> SEQ ID NO 29
<211> LENGTH: 23
<212> TYPE: DNA
<213> ORGANISM: Unknown
<220> FEATURE:
<223> OTHER INFORMATION: primer based on adeno-associated virus 6

<400> SEQUENCE: 29
gctaccgaca acagcgcgtt tct                                                23

<210> SEQ ID NO 30
<211> LENGTH: 25
<212> TYPE: DNA
<213> ORGANISM: Unknown
<220> FEATURE:
<223> OTHER INFORMATION: primer based on adeno-associated virus 6

<400> SEQUENCE: 30
ccaagaagaa gcaccagtcc aggta                                              25

<210> SEQ ID NO 31
<211> LENGTH: 25
<212> TYPE: DNA
<213> ORGANISM: Unknown
<220> FEATURE:
<223> OTHER INFORMATION: primer based on adeno-associated virus 9

<400> SEQUENCE: 31
tacctggact ggtgcttctt cttgg                                              25

<210> SEQ ID NO 32
<211> LENGTH: 25
<212> TYPE: DNA
<213> ORGANISM: Unknown
<220> FEATURE:
<223> OTHER INFORMATION: primer based on adeno-associated virus 9

<400> SEQUENCE: 32
acctctagtc ctgcaggttt aaacg                                              25

<210> SEQ ID NO 33
<211> LENGTH: 25
<212> TYPE: DNA
<213> ORGANISM: Unknown
<220> FEATURE:
<223> OTHER INFORMATION: primer based on adeno-associated virus 9

<400> SEQUENCE: 33
```

```
agacgcggaa gcttcgatca actac                                          25

<210> SEQ ID NO 34
<211> LENGTH: 23
<212> TYPE: DNA
<213> ORGANISM: Unknown
<220> FEATURE:
<223> OTHER INFORMATION: primer based on adeno-associated virus 9

<400> SEQUENCE: 34
ggattcatya gycggtccag gct                                            23

<210> SEQ ID NO 35
<211> LENGTH: 23
<212> TYPE: DNA
<213> ORGANISM: Unknown
<220> FEATURE:
<223> OTHER INFORMATION: primer based on adeno-associated virus 6

<400> SEQUENCE: 35
agcctggacc grctratgaa tcc                                            23

<210> SEQ ID NO 36
<211> LENGTH: 23
<212> TYPE: DNA
<213> ORGANISM: Unknown
<220> FEATURE:
<223> OTHER INFORMATION: primer based on adeno-associated virus 6

<400> SEQUENCE: 36
acagccatgt tagctggaga ccc                                            23

<210> SEQ ID NO 37
<211> LENGTH: 23
<212> TYPE: DNA
<213> ORGANISM: Unknown
<220> FEATURE:
<223> OTHER INFORMATION: primer based on adeno-associated virus 9

<400> SEQUENCE: 37
gggtctccag ctaacatggc tgt                                            23

<210> SEQ ID NO 38
<211> LENGTH: 25
<212> TYPE: DNA
<213> ORGANISM: Unknown
<220> FEATURE:
<223> OTHER INFORMATION: primer based on adeno-associated virus 9

<400> SEQUENCE: 38
acctctagtc ctgcaggttt aaacg                                          25
```

COMPOSITIONS FOR TARGETING CONDUCTING AIRWAY CELLS COMPRISING ADENO-ASSOCIATED VIRUS CONSTRUCTS

CROSS-REFERENCE TO RELATED APPLICATIONS

This is a national stage application under 35 U.S.C. 371 of PCT/US2010/032943, filed on Apr. 29, 2010 which claims the benefit under 35 USC 119(e) of U.S. Patent Application No. 61/174,149, which was filed on Apr. 30, 2009.

STATEMENT REGARDING FEDERALLY SPONSORED RESEARCH OR DEVELOPMENT

This invention was made with government support under grant number HL051746 awarded by the National Institutes of Health. The government has certain rights in the invention.

BACKGROUND OF THE INVENTION

Adeno-associated virus (AAV), a member of the Parvovirus family, is a small nonenveloped, icosahedral virus with a single-stranded linear DNA genome of 4.7 kilobases (kb) to 6 kb. AAV is assigned to the genus, *Dependovirus*, because the virus was discovered as a contaminant in purified adenovirus stocks. AAV's life cycle includes a latent phase at which AAV genomes, after infection, are integrated into host genomes and an infectious phase in which, following either adenovirus or herpes simplex virus infection, the integrated AAV genomes are subsequently rescued, replicated, and packaged into infectious viruses. The properties of non-pathogenicity, broad host range of infectivity, including non-dividing cells, and integration make AAV an attractive delivery vehicle.

The capsid of an AAV contains 60 copies (in total) of three viral proteins (VPs), VP1, VP2, and VP3, in a predicted ratio of 1:1:10, arranged with T=1 icosahedral symmetry [H-J Nam, et al. *J. Virol.*, 81(22): 12260-12271 (November 2007)]. The three VPs are translated from the same mRNA, with VP1 containing a unique N-terminal domain in addition to the entire VP2 sequence at its C-terminal region [Nam et al. cited above]. VP2 contains an extra N-terminal sequence in addition to VP3 at its C terminus. In X-ray crystal structures of the AAV2 [Q. Xie, et al., *Proc Natl. Acad. Sci. USA* 99:10405-10410 (2002)] and AAV4 [L. Govindasamy, et al., *J. Virol.*, 80:11556-11570] capsids and all other structures determined for parvovirus capsids, only the C-terminal polypeptide sequence in the AAV capsid proteins (~530 amino acids) is observed. The N-terminal unique region of VP1, the VP1-VP2 overlapping region, and the first 14 to 16 N-terminal residues of VP3 are disordered [L. Govindasamy, et al., and Q. Xie et al., cited above]. Cryoelectron microscopy and image reconstruction data suggest that in intact AAV capsids, the N-terminal regions of the VP1 and VP2 proteins are located inside the capsid [E. Padron, et al., *J. Virol.* 79:5047-5058 (2005); Q. Xie et al. cited above) and are inaccessible for receptor and antibody binding [S. Kronenberg, et al., *J. Virol.*, 79:5296-5303 (2005)]. Thus, receptor attachment and transduction phenotypes are believed to be determined by the amino acid sequences within the common C-terminal domain of VP1-VP3 [Nam et al., cited above]. The VP1 unique region has been shown to harbor a functional phospholipase A2 enzyme required for endosomal escape during trafficking to the nucleus after receptor attachment, in addition to containing nuclear localization sequences for nuclear targeting [J C Grieger, et al, *J. Virol.* 80:5199-5210 (2006); F., Sonntag, et al, *J. Virol.*, 80:11040-11054 (2006)].

For many years only six AAVs of different sequences were known in the art, with the majority having been isolated as contaminants of adenovirus preparations in cultures. More recently, investigators have described a large number of AAVs of different sequences obtained from tissue [G. Gao, et al., *Proc Natl Acad Sci USA*, 100(10):6081-6086 (May 13, 2003); US-2003-0138772-A1 (Jul. 24, 2003)] and characterized these AAVs into different serotypes and clades [G. Gao, et al., *J. Virol.*, 78(12):6381-6388 (June 2004); International Patent Publication No. WO 2005/033321]. It has been reported that different AAVs exhibit different transfection efficiencies, and also exhibit tropism for different cells or tissues.

Adeno-associated virus serotype 6 (AAV6) can efficiently transduce both the conducting airway epithelium of the mouse lung and human airway epithelial (HAE) cell cultures. C L Halbert et al., "Adeno-associated virus Type 6 (AAV6) Vectors Mediate Efficient Transduction of Airway Epithelial Cells in Mouse Lungs Compared to That of AAV2 Vectors", *J. Virol.*, 75(14): 6615-6624 (July 2001). See also, C L Halbert et al, *J Virol*, 74(3): 1524-1532 (February 2000) (comparing various pseudotypes of AAV2/6, AAV2/3 and AAV2) and E A Rutledge et al, *J Virol*, 72(1): 309-319 (January 1998) (comparing infectious clones from AAV6, AAV2, AAV3 and AAV4). The transduction efficiencies of vectors based on a number of new AAV sequences has also been assessed in mouse airway epithelium in vivo and human ciliated airway epithelium in vitro. [M P Limberis et al., Molecular Therapy, 17(2):294-301 (February 2009).] While three vectors showed efficient transduction in the mouse lung, the high transduction observed in mouse was reproducible in the human cells for only two of the vectors.

Delivery of therapeutic genes to the diseased airway epithelium in vivo is a promising option for the genetic treatment of various lung diseases that include cystic fibrosis (CF) airway disease, a-1-antitrypsin (AAT) deficiency, chronic obstructive pulmonary disease and pulmonary hypertension [M K Aneja and C Rudolph, *Curr Opin Mol Ther*, 8: 432-438 (2006); P E Cruz et al, *Pharmacogenomics*, 8: 1191-1198 (2007); T R Flotte et al, *Mol Ther*, 15: 229-241 (2007)]. However, at present, a safe and efficacious therapeutic vector remains elusive.

SUMMARY OF THE INVENTION

The present invention provides an isolated peptide which permits modification of AAV capsids to preferentially target the conducting airway cells of the lung as well as alveolar epithelial cells, in preference to other, non-lung cells.

In one aspect, the invention provides an artificial AAV capsid comprising a heterologous airway conducting targeting peptide derived from the capsid region from variable loop region IV and V of an AAV Clade A capsid. In one embodiment, the Clade A capsid is selected from AAV1, AAV6 and hu48R3.

In another aspect, the invention provides an AAV vector having an artificial capsid as described and an expression cassette packaged in the capsid.

In still another aspect, the invention provides a conducting airway targeting moiety comprising an artificial AAV capsid as defined, wherein the artificial AAV capsid is linked to a molecule for delivery to the airway conducting epithelium. In yet another aspect, the invention provides a pharmaceutical composition comprising the airway targeting moiety and a physiologically compatible carrier.

In a further aspect, the invention provides a method of altering the specificity of a parental AAV which does not natively target conducting airway cells to provide it with the ability to target conducting airway cells. In another aspect, the invention provides a method of altering the specificity of a parental AAV which does not natively target conducting alveolar epithelium cells to provide it with the ability to target these cells.

In still a further aspect, the invention provides a host cell in culture comprising an artificial AAV capsid or an AAV vector comprising same.

In another aspect, the invention provides a composition comprising an AAV vector and a physiologically compatible carrier.

In yet a further aspect, the invention provides a method of preferentially targeting conducting airway cells and alveolar epithelium cells in preference to non-lung cells. The method involves contacting the cell with an AAV vector as described herein.

In still another aspect, the invention provides a method for treating cystic fibrosis (CF) airway disease, a-1-antitrypsin (AAT) deficiency, chronic obstructive pulmonary disease (COPD) and pulmonary hypertension by delivering a targeting moiety or an AAV vector having an artificial capsid as described herein to a subject in need thereof.

This and other advantages of the present invention will be readily apparent from the following detailed description of the invention.

BRIEF DESCRIPTION OF THE DRAWINGS

FIG. 1A is a schematic of the AAV capsid sequence showing the VP1 and VP2 unique regions and the nine putative variable loop domains. Swaps made are indicated by A-F. FIG. 1B is a diagram of generation of individual fragments via PCR, with reference to the regions identified in FIG. 1A. FIG. 1C is a diagram of the splicing by overlap extension (SOE) reactions, which occurred between the fragments generated as illustrated in FIG. 18 in the presence of external primers.

FIG. 2 is an alignment of the amino acid sequences of the AAV6 [SEQ ID NO:1] and AAV9 [SEQ ID NO:2] capsid, illustrating the locations of the vp1, vp2, vp3, eight β-barrel strands and the nine variable loop domains I, II, II, IV, V, VI, VII, VIII and IX.

DETAILED DESCRIPTION OF THE INVENTION

The present invention provides an isolated peptide which confers conducting airway tropism to AAV capsids which do not natively have this tropism. The conducting airway tropism peptide permits targeting of artificial AAV capsids to conducting airway epithelium as well as aveolar epithelium in preference to non-lung cells and tissues. This is desirable from both a therapeutic and a safety perspective, because the constructs described herein permit more specific targeting of diseased cells and minimize or eliminate transduction of non-target, non-pulmonary cells and tissues.

In one embodiment, the present invention provides an artificial adeno-associated virus capsid comprising a heterologous airway conducting cell targeting peptide. This peptide is derived from the AAV capsid region including variable loop region IV and variable loop region V. As can be readily seen in FIG. 2, the variable loop regions are not immediately adjacent to one another, but have other AAV capsid sequences therebetween. According to the present invention, the heterologous airway conducting cell targeting peptide may further include some of the amino acids from the functional Clade A-AAVs which are located at the amino terminus of variable loop region IV, but which are exclusive of variable loop region III. While there are about 57 amino acids in this region for the functional Clade A-AAVs, the targeting peptide may contain none, one to five amino acids, or some other fragment on the amino terminus of variable loop IV. Further, the heterologous airway conducting cell targeting peptide may further include some of the amino acids from the functional Clade A-AAV which are located at the carboxy terminus of the peptide, but is exclusive of any amino acids of variable loop region VI. While there are about 13 amino acids in this region between loops V and VI for the functional Clade A-AAVs, the peptide may contain 0, 1 to 5, or some other fragment of this region.

In one embodiment, the functional Clade A AAV is selected from AAV1, AAV6, hu44R2, and hu48R3 [WO 2006/110689], all of which share an identical amino acid sequence in this region. An artificial AAV capsid contains this peptide flanked by amino acid residues on the carboxy and/or amino terminus of the AAV variable loop IV and/or variable loop V region which are heterologous to the amino acid sequences which flank this region in the parental AAV.

In one embodiment, the airway conducting cell targeting peptide is designed into the corresponding variable loop region of an AAV capsid which is other than a functional Clade A AAV. The result is an artificial capsid which has a tropism and/or transduction efficiency for conducting airway (and, optionally, alveolar epithelium) which differs from the tropism of the parental (source) AAV. Such an artificial capsid may be generated by a variety of techniques.

As used herein, the "parental AAV capsid" refers to the capsid which has its native tropism modified by the heterologous airway conducting cell targeting peptide as described herein. In one embodiment, the source of the parental AAV capsid sequences is an AAV outside of clade A, as many of the members of this clade have shown some level of conducting airway tropism. Functional clade A AAVs include AAV6, AAV 1, hu44R2, and hu48R3. Other clade A AAVs include hu. 44, hu.46, hu.43, and hu.48, amongst others [WO 2005/033321 and WO 2006/110689].

The other AAV clades include Clade B (represented by AAV2), Clade C (represented by the AAV2-AAV3 hybrid), Clade D (represented by AAV7), Clade E (represented by AAV8), and Clade F (represented by human AAV9). Previously described AAV3, AAV5, and rh32/33 and rh34 are clearly distinct from one another, but were not detected in the screen described herein, and have not been included in any of these clades. Further discussion of AAV clades is provided in G. Gao, et al., *J. Virol.,* 78(12):6381-6388 (June 2004) and International Patent Publication Nos. WO 2004/028817 and WO 2005/033321. The latter document also provides novel human AAV sequences, which are incorporated by reference herein.

However, in another embodiment the parental capsid sequences are from an AAV which natively transduces conducting airway cells at such a level which precludes delivery the AAV to be used as a vector or carrier of any therapeutic or other product.

In one embodiment, the conducting airway targeting peptide is derived from the region including variable loop region IV and variable loop region V of a functional Clade A adeno-associated virus. In one embodiment, the functional Clade A-AAV is selected from AAV1, AAV6, hu44R2 and hu48R3. In one embodiment and with reference to the numbering of the AAV6 capsid, SEQ ID NO:1, this peptide corresponds to about amino acid 447 to about amino acid 521 of the AAV6 capsid of SEQ ID NO:1. Thus, in one embodiment, this targeting peptide has the amino acid sequence: SEQ ID NO:4: NRTQNQSGSAQNKDLLF-SRGSPAGMSVQPKNWLPGPCYRQQRV-SKTKTDNNNS NFTWTGASKYNLNGRESIINPG. Based on the information provided herein regarding AAV6 amino acid locations, one of skill in the art can readily determine corresponding sequences of other Clade A AAV capsid sequences, by aligning the sequences using methods which are known in the art and/or by the crystal structure of the capsids.

In another embodiment, the conducting airway targeting peptide has about one to about eight residues truncated from the amino and/or carboxy terminus of the above peptide. In still another embodiment, the airway conducting cell targeting peptide is a functional fragment within this region, i.e., an internal fragment of this region which confers the desired targeting. Such a fragment may be at least about 65 amino acids in length, at least about 50 amino acids in length, at least about 45 amino acids in length, or shorter. Suitably, such fragments are derived from, with reference to the numbering of the AAV6 capsid (SEQ ID NO:1), variable loop IV range from amino acids 447 to 469, amino acids 447 to 472, amino acid 451 to 469, amino acids 451 to 474. In one embodiment, these fragments are connected to variable loop V sequences from a Clade A AAV. For example, variable loop V may range from amino acids 487 to 521, or 489 to 532 of the Clade A AAV, of may be a fragment thereof which confers the desired targeting (e.g., 487 to 506; 487 to 510; 489 to 506, 487 to 510). In one embodiment, the region range from variable loops IV-V, i.e., amino acids 447 to 510, is used as the conducting airway conducting peptide. In another embodiment, fragments within variable loops IV and V are provided in the chimeric construct, without the connecting AAV6 amino acid sequences. In one embodiment, the chimeric construct contains the variable loop region V of AAV or another Clade A AAV in the absence of other AAV6 capsid sequences (e.g., in the absence of variable loop IV sequences). Based on the information provided herein regarding AAV6 amino acid locations, one of skill in the art can readily determine corresponding sequences of other Clade A AAV capsid sequences, by aligning the sequences and/or by the crystal structure of the capsids.

In yet another embodiment, a chimeric capsid contains the variable loop region 5 of AAV6 or a fragment thereof such as are described herein, in an chimeric capsid, in the absence of other variable loop regions of the Clade A AAV (e.g., AAV6). In still a further embodiment, the chimeric capsid contains at least fragments of both the variable loop regions IV and V of AAV6. Based on the information provided herein regarding AAV6 amino acid locations, one of skill in the art can readily determine corresponding sequences of other Clade A AAV capsid sequences, by aligning the sequences and/or by the crystal structure of the capsids.

In one embodiment the airway conducting airway targeting peptide may be inserted into the corresponding region in the capsid protein of the parent AAV. Given the information provided herein, one of skill in the art can readily locate the corresponding variable region of another AAV (e.g., other than a Clade A AAV). The variable regions herein are consistent with the structural information relating to AAV8 provided in H-J Nam, et al., *J Virol,* 81(22):12260-12271 (November 2007). FIGS. 1-2 herein provide schematic drawings and an exemplary alignment including the AAV6 capsid. Still other capsid protein alignments have been described [see, e.g., WO 03/042397 A1 and WO 2005/033321] or can be prepared.

Typically, when an alignment is prepared based upon the AAV capsid vp1 protein, the alignment contains insertions and deletions which are so identified with respect to a reference AAV sequence (e.g., AAV2 or AAV6) and the numbering of the amino acid residues is based upon a reference scale provided for the alignment. However, any given AAV sequence may have fewer amino acid residues than the reference scale. In the present invention, when discussing the parental AAV and the sequences of the reference library, the term "the same position" or the "corresponding position" refers to the amino acid located at the same residue number in each of the sequences, with respect to the reference scale for the aligned sequences. However, when taken out of the alignment, each of the AAV vp1 proteins may have these amino acids located at different residue numbers.

Alignments are performed using any of a variety of publicly or commercially available Multiple Sequence Alignment Programs. Sequence alignment programs are available for amino acid sequences, e.g., the "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, *Nucl. Acids. Res.*, "A comprehensive comparison of multiple sequence alignments", 27(13):2682-2690 (1999).

There are also a number of algorithms known in the art that can be used to measure nucleotide sequence identity, including those contained in the programs described above. As another example, polynucleotide sequences can be compared using Fasta, a program in GCG Version 6.1. Fasta provides alignments and percent sequence identity of the regions of the best overlap between the query and search sequences. For instance, percent sequence identity between nucleic acid sequences can be determined using Fasta with its default parameters (a word size of 6 and the NOPAM factor for the scoring matrix) as provided in GCG Version 6.1, herein incorporated by reference. Similarly programs are available for performing amino acid alignments. Generally, these programs are used at default settings, although one of skill in the art can alter these settings as needed. Alternatively, one of skill in the art can utilize another algorithm or computer program that provides at least the level of identity or alignment as that provided by the referenced algorithms and programs.

As discussed above, the airway conducting peptide sequence may be located in the native location of corresponding variable loop regions of the heterologous capsid sequence. This may be accomplished through a variety of techniques know to those of skill in the art including e.g., swapping the desired regions using techniques such as those illustrated in the examples herein or know in the art. As illustrated in the examples below, this typically involves excising the corresponding variable loop regions of the heterologous capsid sequence. However, other suitable techniques may be used including, e.g., conventional site-directed mutagenesis techniques on the codon for the amino acid to be altered. Typically, the site-directed mutagenesis is performed using as few steps as required to obtain the desired codon for the conserved amino acid residue. Such methods are well known to those of skill in the art and can be performed using published methods and/or commercially available kits [e.g., available from Stratagene and Promega]. The site-directed mutagenesis may be performed on the AAV genomic sequence. The AAV sequence may be carried by a vector (e.g., a plasmid backbone) for convenience. Alternatively, one of skill in the art can alter the parental AAV using other techniques know to those of skill in the art, e.g., inserting a chemically synthesized peptide, and the like.

In one embodiment, the variable loop regions have been functionally deleted. Optionally, an optional spacer flanks the carboxy and/or the amino terminus of the airway conducting targeting peptide variable. In certain embodiments, the spacer is an exogenous amino acid sequence which is non-native in the sense of not occurring in nature, i.e., being a synthetically or artificially designed or prepared polypeptide. These spacers may comprise one to five amino acids which are derived from a source other than a Clade A capsid or a source other than AAV. In one embodiment, a functional deletion is made in a selected variable loop and no molecule is inserted therein. This may be desired for a variety of reasons, e.g., to accommodate a large insert elsewhere in the capsid. Such a functionally deleted AAV can be utilized to produce an AAV virion, as well as for other uses.

Through the construct of the invention, the native tropism of the AAV or AAV capsid is altered. Hence, by "altered tropism" it is meant that the modified AAV capsid or AAV vector exhibits a target cell binding specificity which is altered, or different, to that of the wild-type virus from which it is derived. Thus, in one embodiment, the invention provides a method of altering the specificity of a selected AAV vector so that it targets conducting airway cells, by providing a heterologous airway conducting cell targeting peptide as described herein. In another embodiment, the targeting peptide further confers the ability to target alveolar epithelium.

In one embodiment, the capsid sequences are provided by a single AAV source. Suitable AAVs may be selected from among AAVs which do not normally transduce conducting airway cells with any efficiency, including, e.g., AAV9, AAV5, AAV2, AAV8, and AAVrh32.22. Still other AAVs may be readily selected from amongst those which have been described [WO 03/042397 A1; WO 2005/033321; WO 2006/110689], and particularly, those AAV which are outside of Clade A. Alternatively, the AAV capsid may be derived from more than one AAV.

In one embodiment, the selected AAV capsid lacks a heparin binding motif. The AAV may be naturally devoid of a heparin binding motif, or the heparin binding motif may be ablated using methods such as those described in WO 2008/027084. Still other modifications to the wild-type AAV sequences may be made, e.g., to enhance production, yield and/or recovery of the artificial capsid protein or an AAV vector having the artificial capsid protein.

The term "functional" refers to a product (e.g., a protein or peptide) which performs its native function, although not necessarily at the same level as the native product. The term "functional" may also refer to a gene which encodes a product and from which a desired product can be expressed. A "functional deletion" refers to a deletion which destroys the ability of the product to perform its native function.

Unless otherwise specified (as above), the term fragments includes peptides at least 8 amino acids in length, at least 15 amino acids in length, at least 25 amino acids in length. However, fragments of other desired lengths may be readily utilized depending upon the desired context. Such fragments may be produced recombinantly or by other suitable means, e.g., by chemical synthesis.

The term "percent (%) identity" may be readily determined for amino acid sequences, over the full-length of a protein, or a fragment thereof. Suitably, a fragment is at least about 8 amino acids in length, and may be up to about 700 amino acids. Generally, when referring to "identity", "homology", or "similarity" between two different adeno-associated viruses, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence.

As used throughout this specification and the claims, the terms "comprise" and "contain" and its variants including, "comprises", "comprising", "contains" and "containing", among other variants, is inclusive of other components, elements, integers, steps and the like. The term "consists of" or "consisting of" are exclusive of other components, elements, integers, steps and the like.

Lung/Conducting Airway Targeting Moiety

In one embodiment, the invention provides an artificial AAV capsid which is an "empty capsid", i.e., a capsid which contains no functional sequences packaged therein. In other words, the capsid lacks an AAV viral genome and/or contains no expression cassette. In one embodiment, the artificial AAV capsid has no functional AAV sequences packaged therein. In another embodiment, the AAV contains no functional AAV gene coding sequences and no endogenous or heterologous expression cassette.

An "empty" AAV capsid may be used as a targeting protein for a heterologous molecule. A desired therapeutic or immunogenic or other molecule may be associated with the artificial AAV capsid of the invention by means of a "linker" sequence.

In one embodiment, chemical cross-linkage between the AAV capsid and the molecule is via covalent or non-covalent linkage. However, other affinity binding pairs may be utilized, as known in the art. Still other conjugation chemistries known in the art are contemplated and may be used in embodiments herein, including but not limited to activated polyethylene glycol (PEG), maleimide or succinimide ester based cross-linkers or SATA-SMCC bifunctional cross-linkers, among other linkages known to those of skill in the art. In a further embodiment, the molecule of interest may be linked to the empty AAV capsid by a PEG linker ('spacer'), as described in Destito, et al., *Chem Biol* 2007 October; 14(10):1152-1162 (2007) and Oh, et al. *Bioconjug Chem* 2006; 17:721-727 (2006).

In another embodiment, the molecule of interest is attached via chemical modification of AAV surface lysine residues using N-hydroxysuccinimide (NHS) esters or sulfhydryl groups using maleimide and haloacetamide reagents, as described in Chatterji, et al., *Bioconj Chem;* 15:807-813 (2004). In yet another embodiment, surface carboxylate groups are modified for specific attachment.

In another embodiment, the molecule of interest may be linked to an AAV capsid via the AAV binding domain of an immunoglobulin molecule. In further embodiments, the binding domain may be an Fab, Fab', $(Fab')_2$, or an Fv fragment of an immunoglobulin molecule. The binding domain may be linked to the molecule of interest by any known means, including those noted above. In one embodiment, a PEG linker is incorporated between the binding domain and the molecule of interest.

Such construction techniques for incorporation of DNA or amino acid sequences, via attachment to a linker sequence, are known in the art and are within the routine skill of a protein/genetic engineer.

Useful molecules for linking to an AAV capsid and delivering to the target cells may include those which are useful for treating conditions such as, e.g., cystic fibrosis, a-1-antitrypsin (AAT) deficiency, chronic obstructive pulmonary disease (COPD), pulmonary hypertension, asthma, lung cancer. Examples of suitable molecules may include non-viral based vectors (e.g., plasmids, "naked-DNA", cosmids, etc) which carry nucleic acids which express gene products. Examples of suitable gene products include those described below in connection with the expression cassettes. Additionally, other non-nucleic acid based molecules may be used in this embodiment, including, e.g., steroids, steroid derivatives, immunomodulatory molecules, enzymes, proteins, small molecules, and other chemical moieties.

In another embodiment, the artificial AAV capsid containing the heterologous airway conducting cell targeting sequence is used in the production of a vector which has packaged therein an expression cassette which delivers a product to the targeted cells.

AAV Vectors with Artificial AAV Capsids Containing Conducting Airway Targeting Domain In one aspect, the invention provides a method of generating a recombinant adeno-associated virus (AAV) having a novel AAV capsid of the invention. Such a method involves culturing a host cell which contains a nucleic acid sequence encoding a novel AAV capsid protein of the invention, or fragment thereof, as defined herein; a functional rep gene; a expression cassette composed of, at a minimum, AAV inverted terminal repeats (ITRs) and a transgene; and sufficient helper functions to permit packaging of the expression cassette into the AAV capsid protein.

The components required to be cultured in the host cell to package an AAV expression cassette in an AAV capsid may be provided to the host cell in trans. Alternatively, one or more of the required components (e.g., expression cassette, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The expression cassette, rep sequences, cap sequences, and helper functions required for producing the rAAV of the invention may be delivered to the packaging host cell in the form of any genetic element which transfer the sequences carried thereon. The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, *J. Virol.,* 70:520-532 (1993) and U.S. Pat. No. 5,478,745.

Unless otherwise specified, the AAV ITRs, and other selected AAV components described herein, may be readily selected from among any AAV, including, without limitation, AAV2, AAV7, AAV9 or another AAV sequences [e.g., WO 03/042397 A1; WO 2005/033321; WO 2006/110689]. These ITRs or other AAV components may be readily isolated using techniques available to those of skill in the art from an AAV sequence. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank®, PubMed®, or the like.

A. The Expression Cassette

The expression cassette is composed of, at a minimum, at least one AAV inverted terminal repeat sequence, a transgene and its regulatory sequences. In one embodiment, both 5' AAV inverted terminal repeats (ITRs) and 3' ITRs are included in the expression cassette. In one desirable embodiment, the expression cassette contains ITRs from an AAV sequence other than those which provided AAV capsid sequences. For example, pseudotyped vectors containing AAV 2 ITRs may be used for convenience. However, ITRs from other suitable sources may be selected. It is this expression cassette that is packaged into a capsid protein and delivered to a selected host cell.

1. The Transgene

The transgene is a nucleic acid sequence, heterologous to the vector sequences flanking the transgene, which encodes a polypeptide, peptide, protein, enzyme, or other product of interest. In one embodiment, the expression cassette carries a nucleic acid sequence, e.g., an RNA. Desirable RNA molecules include tRNA, dsRNA, RNAi, ribosomal RNA, catalytic RNAs, siRNA, small hairpin RNA, trans-splicing RNA, and antisense RNAs. One example of a useful RNA sequence is a sequence which inhibits or extinguishes expression of a targeted nucleic acid sequence in the treated animal. Typically, suitable target sequences include oncologic targets and viral diseases. This may be useful, e.g., for cancer therapies and vaccines.

The nucleic acid coding sequence is operatively linked to regulatory components in a manner which permits transgene transcription, translation, and/or expression in a host cell.

While any variety of products may be delivered using the constructs of the invention, the invention is particularly well suited for delivery of products useful in diagnosis, treatment, and vaccination of conditions associated with conducting airway cells and amelioration of the symptoms thereof. Such conditions include, without limitation, cystic fibrosis, a-1-antitrypsin (AAT) deficiency, chronic obstructive pulmonary disease (COPD) and pulmonary hypertension. Suitable gene products may include a functional cystic fibrosis transmembrane regulator (CFTR) sequence, a-1-antitrypsin, secretory leukoprotease inhibitor, surfactant protein C (SPC), surfactant protein D (SPD), and immunomodulators such as, e.g., interleukins such as interleukin-12, granulocyte macrophase colony stimulating factor (GM-CSF), interferons such as interferon-β, and herpes simplex virus thymidine kinase (HSV-TK). Other gene products may include cancer therapeutics including, e.g., p53, FUS1, RNA, including RNAi, amongst others. Still other suitable expression products can be readily selected by one of skill in the art.

2. Regulatory Elements

In addition to the major elements identified above for the expression cassette, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell,* 41:521-530 (1985)], the SV40 promoter, the dihydrofolate reductase promoter, the β-actin promoter, the phosphoglycerol kinase (PGK) promoter, and the EF1 promoter [Invitrogen]. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied compounds, include, the zinc-inducible sheep metallothionine (MT) promoter, the dexamethasone (Dex)-inducible mouse mammary tumor virus (MMTV) promoter, the T7 polymerase promoter system [International Patent Publication No. WO 98/10088]; the ecdysone insect promoter [No et al, *Proc. Natl. Acad. Sci. USA,* 93:3346-3351 (1996)], the tetracycline-repressible system [Gossen et al, *Proc. Natl. Acad. Sci. USA,* 89:5547-5551 (1992)], the tetracycline-inducible system [Gossen et al, *Science,* 268:1766-1769 (1995), see also Harvey et al, *Curr. Opin. Chem. Biol.,* 2:512-518 (1998)], the RU486-inducible system [Wang et al, *Nat. Biotech.,* 15:239-243 (1997) and Wang et al, *Gene Ther.,* 4:432-441 (1997)] and the rapamycin-inducible system [Magari et al, *J. Clin. Invest.,* 100:2865-2872 (1997)]. Other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the transgene includes a gene operably linked to a tissue-specific promoter. For example, promoters specific for pulmonary tissue and, where available, specific for conducting airway cells, may be used. Examples of such promoters may include, e.g., the forkhead box J1 (FOXJ1) promoter, polyubiquitin promoter UbC, SAM pointed domain-containing ETS transcription factor (SPDEF) promoter, Clara cell secretory protein/uteroglobin (CCSP/UG) promoter, amongst others. Other lung-specific gene promoters may include, e.g., the surfactant protein B (SPB), surfactant protein C (SPC), and surfactant protein A (SPA), ectogenic human carcinoembryonic antigen (CEA) promoter, Thyroid transcription factor 1 (TTF1) and human surfactant protein A1 (hSPA1), amongst others.

Optionally, plasmids carrying therapeutically useful transgenes may also include selectable markers or reporter genes that include sequences encoding geneticin, hygromicin or purimycin resistance, among others. Such selectable reporters or marker genes (preferably located outside the viral genome to be rescued by the method of the invention) can be used to signal the presence of the plasmids in bacterial cells, such as ampicillin resistance. Other components of the plasmid may include an origin of replication. Selection of these and other promoters and vector elements are conventional and many such sequences are available.

The combination of the transgene, promoter/enhancer, and AAV ITRs is referred to as an expression cassette for ease of reference herein. Having been provided with the teachings in this specification, the design of such an expression cassette can be made by resort to conventional techniques.

3. Delivery of the Expression Cassette to a Packaging Host Cell

The expression cassette can be carried on any suitable vector, e.g., a plasmid, which is delivered to a packaging host cell. The plasmids useful in this invention may be engineered such that they are suitable for replication and, optionally, integration in prokaryotic cells, mammalian cells, or both. These plasmids (or other vectors carrying the 5' AAV ITR-heterologous molecule-3' AAV ITR) contain sequences permitting replication of the expression cassette in eukaryotes and/or prokaryotes and selection markers for these systems. Selectable markers or reporter genes may include sequences encoding geneticin, hygromicin or purimycin resistance, among others. The plasmids may also contain certain selectable reporters or marker genes that can be used to signal the presence of the vector in bacterial cells, such as ampicillin resistance. Other components of the plasmid may include an origin of replication and an amplicon, such as the amplicon system employing the Epstein Barr virus nuclear antigen. This amplicon system, or other similar amplicon components, permit high copy episomal replication in the cells. Preferably, the molecule carrying the expression cassette is transfected into the cell, where it may exist transiently. Alternatively, the expression cassette (carrying the 5'AAV ITR-heterologous molecule-3' ITR) may be stably integrated into the genome of the host cell, either chromosomally or as an episome. In certain embodiments, the expression cassette may be present in multiple copies, optionally in head-to-head, head-to-tail, or tail-to-tail concatamers. Suitable transfection techniques are known and may readily be utilized to deliver the expression cassette to the host cell.

Generally, when delivering the vector comprising the expression cassette by transfection, the vector is delivered in an amount from about 5 μg to about 100 μg DNA, about 10 μg to about 50 μg DNA to about $1 \times 10^4$ cells to about $1 \times 10^{13}$ cells, or about $1 \times 10^5$ cells. However, the relative amounts of vector DNA to host cells may be adjusted by one of ordinary skill in the art, who may take into consideration such factors as the selected vector, the delivery method and the host cells selected.

B. Rep and Cap Sequences

In addition to the expression cassette, the host cell contains the sequences which drive expression of a novel AAV capsid protein of the invention (or a capsid protein comprising a fragment thereof) in the host cell and rep sequences of the same source as the source of the AAV ITRs found in the expression cassette, or a cross-complementing source. The AAV cap and rep sequences may be independently obtained from an AAV source as described above and may be introduced into the host cell in any manner known to one in the art as described above. Additionally, when pseudotyping an AAV vector, the sequences encoding each of the essential rep proteins may be supplied by different AAV sources (e.g., AAV2, AAV3, AAV4, AAV5, AAV7, AAV8, AAV9, or one of the other AAV sequences described herein or known in the art). For example, the rep78/68 sequences may be from AAV2, whereas the rep52/40 sequences may be from AAV8.

In one embodiment, the host cell stably contains the capsid protein under the control of a suitable promoter, such as those described above. Most desirably, in this embodiment, the capsid protein is expressed under the control of an inducible promoter. In another embodiment, the capsid protein is supplied to the host cell in trans. When delivered to the host cell in trans, the capsid protein may be delivered via a plasmid which contains the sequences necessary to direct expression of the selected capsid protein in the host cell. Most desirably, when delivered to the host cell in trans, the plasmid carrying the capsid protein also carries other sequences required for packaging the rAAV, e.g., the rep sequences.

In another embodiment, the host cell stably contains the rep sequences under the control of a suitable promoter, such as those described above. Most desirably, in this embodiment, the essential rep proteins are expressed under the control of an inducible promoter. In another embodiment, the rep proteins are supplied to the host cell in trans. When delivered to the host cell in trans, the rep proteins may be delivered via a plasmid which contains the sequences necessary to direct expression of the selected rep proteins in the host cell.

Thus, in one embodiment, the rep and cap sequences may be transfected into the host cell on a single nucleic acid molecule and exist stably in the cell as an episome. In another embodiment, the rep and cap sequences are stably integrated into the chromosome of the cell. Another embodiment has the rep and cap sequences transiently expressed in the host cell. For example, a useful nucleic acid molecule for such transfection comprises, from 5' to 3', a promoter, an optional spacer interposed between the promoter and the start site of the rep gene sequence, an AAV rep gene sequence, and an AAV cap gene sequence.

Optionally, the rep and/or cap sequences may be supplied on a vector that contains other DNA sequences that are to be introduced into the host cells. For instance, the vector may contain the rAAV construct comprising the expression cassette. The vector may comprise one or more of the genes encoding the helper functions, e.g., the adenoviral proteins E1, E2a, and E4 ORF6, and the gene for VAI RNA.

Preferably, the promoter used in this construct may be any of the constitutive, inducible or native promoters known to one of skill in the art or as discussed above. In one embodiment, an AAV P5 promoter sequence is employed. The selection of the AAV to provide any of these sequences does not limit the invention.

In another preferred embodiment, the promoter for rep is an inducible promoter, such as are discussed above in connection with the transgene regulatory elements. One preferred promoter for rep expression is the T7 promoter. The vector comprising the rep gene regulated by the T7 promoter and the cap gene, is transfected or transformed into a cell which either constitutively or inducibly expresses the T7 polymerase. See International Patent Publication No. WO 98/10088, published Mar. 12, 1998.

The spacer is an optional element in the design of the vector. The spacer is a DNA sequence interposed between the promoter and the rep gene ATG start site. The spacer may have any desired design; that is, it may be a random sequence of nucleotides, or alternatively, it may encode a gene product, such as a marker gene. The spacer may contain genes which typically incorporate start/stop and polyA sites. The spacer may be a non-coding DNA sequence from a prokaryote or eukaryote, a repetitive non-coding sequence, a coding sequence without transcriptional controls or a coding sequence with transcriptional controls. Two exemplary sources of spacer sequences are the phage ladder sequences or yeast ladder sequences, which are available commercially, e.g., from Gibco or Invitrogen, among others. The spacer may be of any size sufficient to reduce expression of the rep78 and rep68 gene products, leaving the rep52, rep40 and cap gene products expressed at normal levels. The length of the spacer may therefore range from about 10 bp to about 10.0 kbp, preferably in the range of about 100 bp to about 8.0 kbp. To reduce the possibility of recombination, the spacer is preferably less than 2 kbp in length; however, the invention is not so limited.

Although the molecule(s) providing rep and cap may exist in the host cell transiently (i.e., through transfection), it is preferred that one or both of the rep and cap proteins and the promoter(s) controlling their expression be stably expressed in the host cell, e.g., as an episome or by integration into the chromosome of the host cell. The methods employed for constructing embodiments of this invention are conventional genetic engineering or recombinant engineering techniques such as those described in the references above. While this specification provides illustrative examples of specific constructs, using the information provided herein, one of skill in the art may select and design other suitable constructs, using a choice of spacers, P5 promoters, and other elements, including at least one translational start and stop signal, and the optional addition of polyadenylation sites.

In another embodiment of this invention, the rep or cap protein may be provided stably by a host cell.

C. The Helper Functions

The packaging host cell also requires helper functions in order to package the rAAV of the invention. Optionally, these functions may be supplied by a herpesvirus. Most desirably, the necessary helper functions are each provided from a human or non-human primate adenovirus source, such as those described above and/or are available from a variety of sources, including the American Type Culture Collection (ATCC), Manassas, Va. (US). In one currently preferred embodiment, the host cell is provided with and/or contains an E1a gene product, an E1b gene product, an E2a gene product, and/or an E4 ORF6 gene product. The host cell may contain other adenoviral genes such as VAI RNA, but these genes are not required. In a preferred embodiment, no other adenovirus genes or gene functions are present in the host cell.

The adenovirus E1a, E1b, E2a, and/or E4ORF6 gene products, as well as any other desired helper functions, can be provided using any means that allows their expression in a cell. Each of the sequences encoding these products may be on a separate vector, or one or more genes may be on the same vector. The vector may be any vector known in the art or disclosed above, including plasmids, cosmids and viruses. Introduction into the host cell of the vector may be achieved by any means known in the art or as disclosed above, including transfection, infection, electroporation, liposome delivery, membrane fusion techniques, high velocity DNA-coated pellets, viral infection and protoplast fusion, among others. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by other means, e.g., by exogenously added factors.

D. Host Cells and Packaging Cell Lines

The host cell itself may be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, BHK, MDCK, COS 1, COS 7, BSC 1, BSC 40, BMT 10, VERO, WI38, HeLa, 293 cells (which express functional adenoviral E1), Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc. The requirements for the cell used is that it not carry any adenovirus gene other than E1, E2a and/or E4 ORF6; it not contain any other virus gene which could result in homologous recombination of a contaminating virus during the production of rAAV; and it is capable of infection or transfection of DNA and expression of the transfected DNA. In a preferred embodiment, the host cell is one that has rep and cap stably transfected in the cell.

One host cell useful in the present invention is a host cell stably transformed with the sequences encoding rep and cap, and which is transfected with the adenovirus E1, E2a, and E4 ORF6 DNA and a construct carrying the expression cassette as described above. Stable rep and/or cap expressing cell lines, such as B-50 (International Patent Application Publication No. WO 99/15685), or those described in U.S. Pat. No. 5,658,785, may also be similarly employed. Another desirable host cell contains the minimum adenoviral DNA which is sufficient to express E4 ORF6. Yet other cell lines can be constructed using the novel singleton-corrected AAV cap sequences of the invention.

The preparation of a host cell according to this invention involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus and AAV genomes, combined with polymerase chain reaction, synthetic methods, and any other suitable methods which provide the desired nucleotide sequence.

Introduction of the molecules (as plasmids or viruses) into the host cell may also be accomplished using techniques known to the skilled artisan and as discussed throughout the specification. In preferred embodiment, standard transfection techniques are used, e.g., $CaPO_4$ transfection or electroporation, and/or infection by hybrid adenovirus/AAV vectors into cell lines such as the human embryonic kidney cell line HEK 293 (a human kidney cell line containing functional adenovirus E1 genes which provides trans-acting E1 proteins).

Pharmaceutical Compositions and Uses Therefor

Pharmaceutical compositions containing an airway targeting molecule are described herein, which comprise an artificial AAV capsid linked to a moiety for delivery to the airway conducting epithelium and a physiologically compatible carrier. Other pharmaceutical compositions contain an AAV vector containing an artificial AAV capsid as described herein with a physiologically compatible carrier. These compositions are well suited for preferentially targeting conducting airway cells and for targeting alveolar epithelial, in preference to non-lung, cells. In one embodiment, these compositions are formulated with a carrier suitable for intranasal, oral or intratracheal delivery. However, other formularies and delivery routes may be selected.

Recombinant vectors containing the artificial AAV capsid may be delivered to host cells according to published methods. The rAAV, preferably suspended in a physiologically compatible carrier, may be administered to a human or non-human mammalian patient. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water.

Optionally, the compositions may contain, in addition to the AAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The vectors or AAV targeting moieties are administered in sufficient amounts to provide a therapeutic benefit without undue adverse effects, or with medically acceptable physiological effects, which can be determined by those skilled in the medical arts. Conventional and pharmaceutically acceptable routes of administration include, but are not limited to, direct delivery to a desired organ (e.g., the lung), oral, inhalation, intranasal, intratracheal, intraarterial, intraocular, intravenous, intramuscular, subcutaneous, intradermal, and other parental routes of administration. Routes of administration may be combined, if desired.

Dosages of the viral vector or targeting moiety will depend primarily on factors such as the condition being treated, the age, weight and health of the patient, and may thus vary among patients. For example, a therapeutically effective human dosage of the viral vector is generally in the range of from about 0.1 mL to about 100 mL of solution containing concentrations of from about $1 \times 10^9$ to $1 \times 10^{16}$ genomes virus vector. A preferred human dosage for delivery to large organs (e.g., liver, muscle, heart and lung) may be about $5 \times 10^{10}$ to $5 \times 10^{13}$ AAV genomes, at a volume of about 1 to 100 mL. A preferred dosage for delivery to eye is about $5 \times 10^9$ to $5 \times 10^{12}$ genome copies, at a volume of about 0.1 mL to 1 mL. For example, a therapeutically effective human dosage of an airway conducting cell targeting moiety is generally in the range of about 100 mg to about 10 mg of the moiety. This may be delivered in solution, e.g., in about 0.1 mL to about 100 mL of solution. For both the viral vector and the targeting moiety, the dosage may be adjusted to balance the therapeutic benefit against any side effects and such dosages may vary depending upon the therapeutic application for which the recombinant vector is employed. The levels of expression of the transgene and/or the circulating half-life of a therapeutic or vaccinal molecule can be monitored to determine the frequency of dosage. Optionally, dosage regimens similar to those described for therapeutic purposes may be utilized for immunization using the compositions of the invention.

Examples of therapeutic products and immunogenic products for delivery by the AAV-derived constructs of the invention are provided below. These constructs may be used for a variety of therapeutic or vaccinal regimens, as described herein. Additionally, these vectors may be delivered in combination with one or more other vectors or active ingredients in a desired therapeutic and/or vaccinal regimen.

EXAMPLES

The following examples are illustrative only and are not a limitation on the present invention.

Example 1

AAV Having AAV6/9 Chimeric Capsid

A. Construction of AAV Chimera with Variable Loop Regions IV-V

Figure 1B:
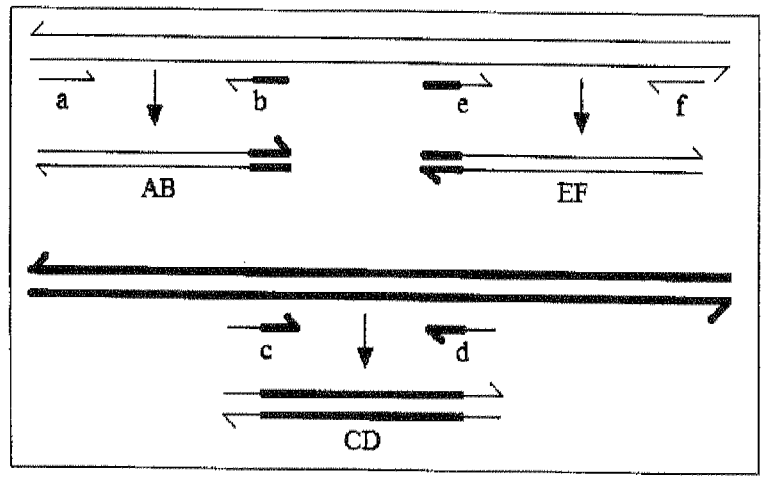
Figure 1C:
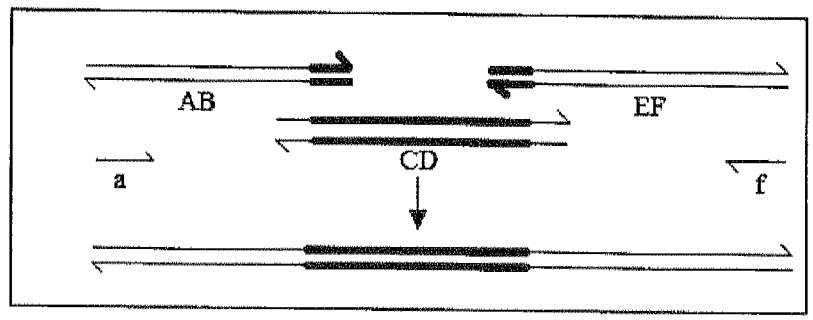
Figure 2:
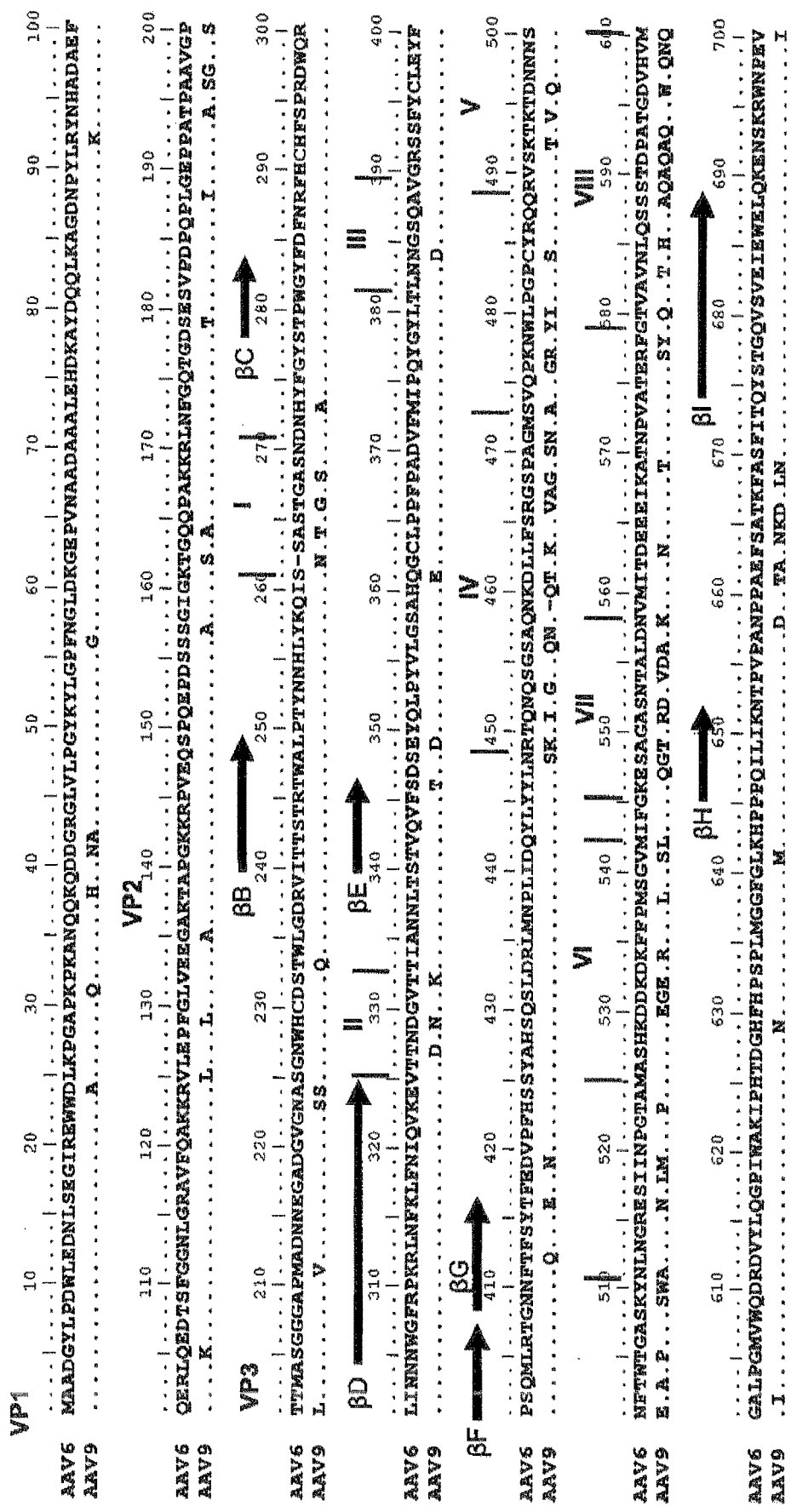

Specific domains of the AAV6 and AAV9 capsid were swapped using PCR splicing by overlap extension (FIGS. 1A-C). This method involves the use of primers to amplify the regions to be swapped in each vector capsid. These primers were designed to have a 5' overhang of 10-15 base pairs complementary to the heterologous capsid sequence so that the ends of the PCR products contain complementary sequences. This allowed the fragments to be joined together in a second PCR reaction using one set of primers complementary to the outer 5' and 3' ends to form the chimeric capsid sequence. F refers to the forward primer and R to the reverse primer.

AAV6 VL IV-V

| | |
|---|---|
| 5'-AGCCTGGACCGRCTATGAATCC-3' | SEQ ID NO: 5<br>F |
| 5'-GCCATAGCAGGTCCAGGGTTGAT-3' | SEQ ID NO: 6<br>R |

AAV9 VP1-VL IV

| | |
|---|---|
| 5'-AGACGCGGAAGCTTCGATCAACTAC-3' | SEQ ID NO: 7<br>F |
| 5'-GGATTCATYAGYCGGTCCAGGCT-3' | SEQ ID NO: 8<br>R |

AAV9 VL V-End

| | |
|---|---|
| 5'-ATCAACCCTGGACCTGCTATGGC-3' | SEQ ID NO: 9<br>F |
| 5'-ACCTCTAGTCCTGCAGGTTTAAACG-3' | SEQ ID NO: 10<br>R |

Twelve chimeras were constructed, which included swaps of the VP1 and VP2 unique regions and the nine putative surface variable loop regions of the capsid.

These chimeric capsid sequences were then cloned into a plasmid containing the AAV2 rep gene by restriction site digestion and then transfected into 293 cells, along with a plasmid containing GFP expressed from a cytomegalovirus (CMV) promoter and flanked by the AAV2 inverted terminal repeats (ITR) plus an AdV helper plasmid. Six of these vectors were progressed to large scale preparation and purification expressing either GFP from a CMV promoter or nLacZ from a chicken β-actin (CB) promoter. Vector titers were determined by TaqMan real-time PCR using bovine growth hormone (bGH) polyA-specific primers and probe.

B. Transduction of Human Airway Epithelial Cell Cultures

The transduction profiles of these six vectors were then examined on human airway epithelial (HAE) cell cultures to determine their ability to transduce human conducting airway [T E Gray, et al. *Am J Respir Cell Mol Biol*, 14: 104-12 (1996)]. Primary HAE cells (Lonza) were seeded at ~50,000 cells/well on 24-well transwell plates. Once fully confluent, these cells were grown at air-liquid interface for at least 4 weeks before used in experiments to allow proper cell differentiation. To examine AAV transduction of HAE cells, the six AAV chimeras, plus AAV2/6 and AAV2/9 as controls, expressing GFP were added to the apical surface of the HAE cells at $1 \times 10^{11}$ genome copies (GC)/well in 50 μl. Vector was removed 2 hours later and the cells were maintained at air-liquid interface. GFP expression was evaluated five days later.

This experiment revealed that swapping variable loop regions IV-V of the AAV6 capsid (amino acid 447-521 of SEQ ID NO:1) into the AAV9 capsid (AAV2/9-6VL IV-V) conferred transduction similar to that of AAV6, whereas AAV9 does not normally transduce conducting airway. Conversely, swapping the homologous region of AAV9 into the AAV6 capsid (AAV2/6-9VL IV-V) ablated AAV6's ability to transduce HAE cells efficiently. This indicates that this domain of the AAV6 capsid is important for conducting airway tropism. Additionally, this phenomenon is specific to variable loop regions IV-V of AAV6 because the same results were not observed for the other chimeras.

C. In Vivo Transduction of Murine Lung

The transduction profiles of these vectors were also examined in the mouse lung after intranasal instillation. $1 \times 10^{11}$ GC of each chimera expressing nLacZ, plus AAV2/6 and AAV2/9 as controls, was delivered intranasally to C57Bl/6 mice in 50 μl total volume phosphate buffered saline (PBS). Twenty-one days later, the lungs were inflated with a 1:1 mixture of optimal cutting temperature (OCT) compound and PBS, removed and frozen in OCT for sectioning and staining for β-gal expression.

Again, swapping variable loop regions IV-V of the AAV6 capsid into the AAV9 capsid was observed to confer a novel tropism on AAV9 for the conducting airway epithelium. And conversely, swapping the homologous region of AAV9 into the AAV6 capsid ablated AAV6 transduction.

Taken together, these studies indicate that a domain of the AAV6 capsid important for conducting airway transduction has been identified. Variable loop regions IV-V (amino acids 447-521 of AAV6) are located on surface-exposed protrusions of the icosahedral threefold axis of the capsid and may determine cellular interactions necessary for transduction.

Example 2

AAV6/9 Chimera Having AAV6 Narrow VL IV and Narrow VL V in AAV9 Capsid

A. Construction of AAV Chimera with Variable Loop Regions IV-V

Narrow fragments of the AAV6 variable loop IV and variable loop V were inserted into the AAV9 capsid from which the corresponding regions of AAV9 were removed using PCR splicing by overlap extension, using the methods described in Example 1. F refers to the forward primer and R to the reverse primer.

AAV9 VP1-VL IV Narrow

```
                                        SEQ ID NO: 11
5-'AGACGCGGAAGCTTCGATCAACTAC-3'              F

SEQ ID NO: 12
5'-TCCGGACTGATTCTG/AGTCTTTGAGAGAT-3'         R
```

AAV6 VL IV Narrow

```
                                        SEQ ID NO: 13
5'-ATCTCTCAAAGACT/CAGAATCAGTCCGGA-3'         F

SEQ ID NO: 14
5'-ACAGCCATGTT/AGCTGGAGACCC-3'               R
```

AAV9 VL IV Narrow-VL V Narrow

```
                                        SEQ ID NO: 15
5'-GGGTCTCCAGCT/AACATGGCTGT-3'               F

SEQ ID NO: 16
5'-TAGAAACGCGCTGTTGTCGGTAGCTGG-3'            R
```

AAV6 VL V Narrow

```
                                        SEQ ID NO: 17
5'-GCTACCGACAACAGCGCGTTTCT-3'                F

SEQ ID NO: 18
5'-CCAAGAAGAAGC/ACCAGTCCAGGTA-3'             R
```

AAV9 VL V Narrow-End

```
                                        SEQ ID NO: 19
5'-TACCTGGACTGGT/GCTTCTTCTTGG-3'             F

SEQ ID NO: 20
5'-ACCTCTAGTCCTGCAGGTTTAAACG-3'              R
```

The narrow AAV6VL-IV narrow corresponds to amino acid sequences 450-469 of SEQ ID NO: 1. The narrow AAV6VL-V narrow corresponds to amino acid sequences 487-505 of SEQ ID NO: 1. The resulting chimeric capsid contains AAV9 capsid sequences flanking both the amino and carboxy teriminus of each of the AAV6 variable loop regions, including the amino acid sequences located between the carboxy terminus of the AAV6VL-IV narrow and the amino terminus of the AAV6VL-V narrow.

The constructed chimeric capsid sequences were cloned into a plasmid containing the AAV2 rep gene by restriction site digestion and then transfected into 293 cells in six-well plates, along with a plasmid containing firefly luciferase (ffluc) expressed from a cytomegalovirus (CMV) promoter and flanked by the AAV2 inverted terminal repeats (ITR) plus an AdV helper plasmid. Media was changed one day after transfection and cell lysate was collected three days after transfection. Lysates were freeze/thawed three times and spun down to remove cell debris. Vector genome copies (GC) were then titered by quantitative PCR using SV40 polyA-specific primers and probe.

The resulting chimeric AAV viral particle carrying the ffluc expression cassette showed titers at a level of about $1 \times 10^{11}$ genome copies/mL, which is intermediate between the titers observed for AAV2/6 and AAV2/9 controls which contained the same expression cassettes, but intact AAV6 or AAV9 capsids, respectively.

To examine in vitro transduction, 293 cells were seeded at $1 \times 10^5$ cells/well in 96-well plates. $1 \times 10^9$ GC of each vector was added to the cells in triplicate in 100 ul total volume of media. After overnight incubation, the vector was removed and replaced with fresh media. 72 hours after transduction, ffluc expression was examined by luminescence imaging.

One chimeric construct made as described above, AAV2/9-having a narrow variable loop IV region and a narrow variable loop V region (amino acids 487-505 of AAV 6) was tested at small scale titer and for in vitro transduction in 293 cells. Titers of about $1 \times 10^{11}$ genome copies/mL were observed; these titers are higher than those observed for the AAV2/6 control, but lower than the AAV2/9 control observed. In vitro transduction levels for the chimeric AAV2/9-having an AAV6 variable loop IV region and a narrow variable loop V region were lower than those observed for AAV2/6, but higher than those of AAV2/9.

The results showed transduction levels for the chimeric AAV6 with the narrow IV and narrow V were slightly higher than AAV2/9, and lower than AAV2/6.

Large scale preparations are being made for these constructs and they will be assessed in murine lung as described in Example 1.

Example 3

AAV6/9 Chimeric Having AAV6 Variable Loop V in AAV9 Capsid

Narrow fragments of the AAV6 variable loop V inserted into the AAV9 capsid (in the absence of AAV6 loop IV) from which the corresponding region of AAV9 are removed using PCR splicing by overlap extension, using the methods described in Example 1. F refers to the forward primer and R to the reverse primer.

One of the chimeric capsid constructs contains only a narrow fragment of variable loop V of AAV6 in the AAV9 capsid: amino acids 1-486 of AAV9, amino acids 487-505 of AAV 6 (SEQ ID NO: 1), and amino acids 487-736 of AAV9. The following primers are utilized for this construct.

AAV6 VL V Narrow Alone Chimera:
AAV9 VP1-VL V Narrow

```
                                          SEQ ID NO: 27
    5'-AGACGCGGAAGCTTCGATCAACTAC-3'            F

SEQ ID NO: 28
    5-'TAGAAACGCGCTGTTGTCGGTAGCTGG-3'          R
```

Other chimeric capsid construct contains both narrow fragments of variable loop V and variable loop IV of AAV6 inserted in the corresponding regions of the AAV9 capsid. AAV6 VL V Narrow (Amplifying the Region Encoding Amino Acids 487-505 of SEQ ID NO:1)

```
                                          SEQ ID NO: 29
    5'-GCTACCGACAACAGCGCGTTTCT-3'              F

SEQ ID NO: 30
    5'-CCAAGAAGAAGC/ACCAGTCCAGGTA-3'           R
```

AAV9 VL V Narrow-End

```
                                          SEQ ID NO: 31
    5'-TACCTGGACTGGT/GCTTCTTCTTGG-3'           F

SEQ ID NO: 32
    5'-ACCTCTAGTCCTGCAGGTTTAAACG-3'            R
```

One chimeric construct, AAV2/9-having a narrow variable loop V region (amino acids 487-505 of AAV 6) was tested at small scale titer and for in vitro transduction in 293 cells. It has a titer slightly lower than AAV2/6 (~3×10¹⁰), but in vitro transduction similar to AAV2/6.

Example 4

AAV6/9 Chimeric Having AAV6 VL IV Fragment in AAV9 Capsid

Modified narrow fragments of the AAV6 variable loop IV are inserted into the AAV9 capsid from which the corresponding region of AAV9 are removed using PCR splicing by overlap extension, using the methods described in Example 1. The following primers are utilized. F refers to the forward primer and R to the reverse primer.

AAV9 VP1-VL IV Broad

```
                                    SEQ ID NO: 33
5'-AGACGCGGAAGCTTCGATCAACTAC-3'           F

SEQ ID NO: 34
5-'GGATTCATYAGYCGGTCCAGGCT-3'             R
```

AAV6 VL IV Broad L and Narrow R (Amplifying the Region Encoding Amino Acids 447-469 of AAV6)

```
                                    SEQ ID NO: 35
5'-AGCCTGGACCGRCTRATGAATCC-3'             F

SEQ ID NO: 36
5'-ACAGCCATGTT/AGCTGGAGACCC-3'            R
```

AAV9 VL IV Narrow-End

```
                                    SEQ ID NO: 37
5'-GGGTCTCCAGCT/AACATGGCTGT-3'            F

SEQ ID NO: 38
5'-ACCTCTAGTCCTGCAGGTTTAAACG-3'           R
```

Poor transduction results were observed for chimeric constructs containing only the AAV6 variable loop IV, or a narrow fragment thereof, in the absence of AAV6 variable loop V. However, another construct, containing additional amino acids at the amino end of the VL IV region have been made. This construct contains AAV6 amino acids 447 to 469.

All publications cited in this specification are incorporated herein by reference. While the invention has been described with reference to a particularly preferred embodiment, it will be appreciated that modifications can be made without departing from the spirit of the invention. Such modifications are intended to fall within the scope of the appended claims.

The invention claimed is:

1. An adeno-associated virus (AAV) vector useful for targeting conducting airway cells, wherein the vector has an AAV capsid and an expression cassette packaged therein, wherein the capsid comprises a chimeric capsid protein comprising an airway conducting cell targeting peptide and at least amino acids (aa) 1 to aa 389 and aa 524 to aa 736 of an AAV9 capsid protein having the amino acid sequence of SEQ ID NO: 2, wherein the airway conducting cell targeting peptide comprises one of (a) to (d):

(a) aa 447 to aa 521 of the amino acid sequence of SEQ ID NO:1;

(b) aa 450 to aa 469 of the amino acid sequence of SEQ ID NO:1 and aa 487 to aa 505 of the amino acid sequence of SEQ ID NO:1;

(c) aa 487 to aa 505 of the amino acid sequence of SEQ ID NO:1; or (d) aa 447 to aa 469 of the amino acid sequence of SEQ ID NO:1;

wherein the airway conducting cell targeting peptide is located in the chimeric capsid protein in a location corresponding to the location of the targeting peptide in the AAV6 capsid protein, wherein the corresponding location of the airway conducting cell targeting peptide location is determined by a sequence alignment between the chimeric capsid protein and the AAV9 capsid protein, and wherein the expression cassette comprises at least one AAV inverted terminal repeat sequence and a heterologous gene operably linked to regulatory sequences which permit expression of the heterologous gene in the conducting airway cells.

2. The AAV vector according to claim 1, wherein the airway conducting cell targeting peptide has the amino acid sequence of SEQ ID NO: 4: NRTQNQSGSAQNKDLLF-SRGSPAGMSVQPKNWLPGPCYRQQRV-SKTKTDNNNSNFTW TGASKYNLNGRESIINPG.

3. The AAV vector according to claim 1, wherein the heterologous gene encodes a product useful for treating or ameliorating the symptoms of cystic fibrosis.

4. The AAV vector according to claim 1, where the heterologous gene encodes a product selected from the group consisting of a functional cystic fibrosis transmembrane regulator (CFTR), an alpha-1 antitrypsin (A1AT), a surfactant protein C (SPC), and a surfactant protein D (SPD).

5. A composition comprising the AAV vector according to claim 1 and a physiologically compatible carrier.

6. An adeno-associated virus (AAV) vector useful for targeting conducting airway cells, wherein the vector has an AAV capsid and an expression cassette packaged therein, wherein the AAV capsid comprises a chimeric capsid protein comprising at least variable loop regions III and VI of a non-Clade-A capsid protein and an airway conducting cell targeting peptide, wherein the variable loop region III of the non-Clade-A capsid protein corresponds to amino acid (aa) 381 to aa 388 of an AAV6 capsid protein having the amino acid sequence of SEQ ID NO: 1 and the variable loop region VI corresponds to amino acids from aa 524 to 541 of the amino acid sequence of SEQ ID NO: 1, wherein the airway conducting cell targeting peptide comprises one of (a) to (d):

(a) aa 447 to aa 521 of the amino acid sequence of SEQ ID NO:1;

(b) aa 450 to aa 469 of the amino acid sequence of SEQ ID NO:1 and aa 487 to aa 505 of the amino acid sequence of SEQ ID NO:1;

(c) aa 487 to aa 505 of the amino acid sequence of SEQ ID NO:1; or (d) aa 447 to aa 469 of the amino acid sequence of SEQ ID NO:1;

wherein the airway conducting cell targeting peptide is located in the chimeric capsid protein in a location corresponding to the location of the targeting peptide in the AAV6 capsid protein, wherein the corresponding location of the airway conducting cell targeting peptide location is determined by a sequence alignment between the chimeric capsid protein and the AAV9 capsid protein, and wherein said expression cassette comprises at least one AAV inverted terminal repeat sequence and a heterologous gene operably linked to regulatory sequences which permit expression of the heterologous gene in the conducting airway cells.

7. The AAV vector according to claim 6, wherein the airway conducting cell targeting peptide has the amino acid sequence of SEQ ID NO: 4: NRTQNQSGSAQNKDLLF-SRGSPAGMSVQPKNWLPGPCYRQQRV-SKTKTDNNNSNFTW TGASKYNLNGRESIINPG.

8. The AAV vector according to claim 6, wherein the heterologous gene encodes a product useful for treating or ameliorating the symptoms of cystic fibrosis.

9. The AAV vector according to claim 6, wherein the heterologous gene encodes a product selected from the group consisting of a functional cystic fibrosis transmembrane regulator (CFTR), an alpha-1 antitrypsin (A1AT), a surfactant protein C (SPC), and a surfactant protein D (SPD).

10. A pharmaceutical composition comprising the AAV vector according to claim 6 and a physiologically compatible carrier.

11. The composition according to claim 10, which is formulated for intranasal, oral or intratracheal delivery.

12. The AAV vector according to claim 6, wherein the airway conducting cell targeting peptide comprises aa 450 to aa 469 of the amino acid sequence of SEQ ID NO:1 and aa 487 to aa 505 of the amino acid sequence of SEQ ID NO:1.

13. The AAV vector according to claim 6, wherein the airway conducting cell targeting peptide comprises aa 487 to aa 505 of the amino acid sequence of SEQ ID NO:1.

14. The AAV vector according to claim 6, wherein the airway conducting cell targeting peptide comprises aa 447 to aa 469 of the amino acid sequence of SEQ ID NO:1.

\* \* \* \* \*